United States Patent [19]

Dall'Asta et al.

[11] Patent Number: 4,950,687
[45] Date of Patent: Aug. 21, 1990

[54] DIACETYLRHEIN SALTS AND THEIR THERAPEUTICAL USE IN THE TREATMENT OF ARTHROSIS

[75] Inventors: Leone Dall'Asta, Pavia; Germano Coppi, Buccinasco; Mario Ercole Scevola, Milan, all of Italy

[73] Assignee: Proter S.p.A., Opera, Italy

[21] Appl. No.: 379,787

[22] Filed: Jul. 17, 1989

Related U.S. Application Data

[63] Continuation-in-part of Ser. No. 45,817, May 4, 1987, abandoned.

[30] Foreign Application Priority Data

May 2, 1986 [IT] Italy .................................. 20298 A/86

[51] Int. Cl.$^5$ ............................................. A01N 37/10
[52] U.S. Cl. ..................................... 514/548; 514/569; 514/903
[58] Field of Search ...................... 514/548, 569, 903; 552/262

[56] References Cited

U.S. PATENT DOCUMENTS 4,244,968  1/1981  Friedman ............................ 552/262
4,346,103  8/1982  Friedman ............................ 514/548

Primary Examiner—Richard L. Raymond
Assistant Examiner—Raymond Covington
Attorney, Agent, or Firm—Cushman, Darby & Cushman

[57] ABSTRACT

A therapeutic treatment for the athrosis diseases comprising administering by intraarticular route from 1 to 5 ml of an aqueous solution containing from 10 to 50 mg of a diacetyl rhein salt having formula (I):

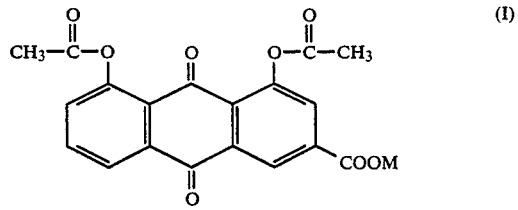

wherein M represents an alkali or an earth alkali metal or the residue of an organic base.

The diacetyl rhein salts administered by intraarticular route exhibit higher pharmacological activity than the corresponding diacetylrhein administered orally.

2 Claims, No Drawings

DIACETYLRHEIN SALTS AND THEIR THERAPEUTICAL USE IN THE TREATMENT OF ARTHROSIS

This application is a continuation-in-part of application Ser. No. 07/045,817, filed May 4, 1987, now abandoned.

FIELD OF THE INVENTION

The present invention relates to a therapeutic method to carry out arthrosis diseases comprising administering by intraarticular route an aqueous solution of diacetyl rhein salts.

BACKGROUND OF THE INVENTION

The diacetyl rhein of formula (II)

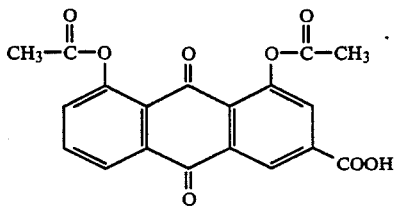

is a drug having antiarthrosis activity and such an activity is claimed by the same Applicant in Italian patent application 1,098,332.

The diacetylrhein used as such has the drawback to be water insoluble, therefore it cannot be administered by parenteral or by intraarticular route. but it can only be given by oral route.

The oral therapeutic method has the disadvantage. that in order to be effective, high amount of diacetylrhein must be administered to the patient affected by artrhosis, and for a long time period.

THE PRESENT INVENTION

Object of the present invention is a therapeutic method for the treatment of arthrosis diseases comprising administering by intraarticular route from 1 to 5 ml of an aqueous solution containing from 10 to 50 mg of diacetylrhein salts having the general formula (I)

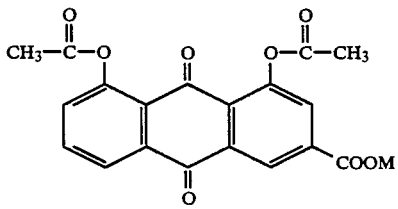

wherein M represents an alkali or an earth alkali metal or the residue of an organic base.

With the therapeutic method according to the present invention, the active principle being administered locally, it is rapidly administer the drug for long time periods and in high amounts, as it occurs in the case of the oral administration of the diacetyl rhein, moreover the activity of the drug is so high by using the therapeutic method according to the present invention, that the time intercurring between an administration and the subsequent is much longer (1 week) than in the case of the diacetyl rhein administered by oral route(1 day).

A preferred embodiment of the therapeutic method according to the present invention comprises administering 2ml of an aqueous solution containing 25 mg of diacetylrhein potassium salts once a week for 5-6 times.

The diacetylrhein salts are prepared by solubilizing the diacetylrhein in a solvent mixture of a water miscible organic solvent and water. The organic solvent is selected among acetone dioxane, dimethylformamide and dimethylacetamide. The water content in the solvent mixture must be of 2-15% by volume.

The resulting solution of diacetylrhein is then added with a calculated amount of an organic base, selected among tertiary amines preferably triethylamine in at least 15by volume excess with respect to the stoichiometrical amount.

In order to obtain a salt of diacetylrhein of an alkali or an earth alkali metal, the salt of diacetylrhein with an organic base is reacted with a salifying agent, i.e. a salt of the desired cation of a weak organic or inorganic acid. Examples of a weak organic acid include 2 ethylhexanoic acid, carbonic acid.

The solubilizing reaction is preferably carried out at the temperature of 15°-20° C. The subsequent precipitation, for instance of the sodium salt of diacetyl rhein, takes place by adding a calculated amount of a solution of sodium 2-ethylhexanoate in a suitable water miscible organic solvent preferably isobutyl alcohol diluted with acetone.

The amount of salifying agent is preferably in excess by 10-15% in excess with respect to the stoichiometric amount.

Likewise the crystallization of the potassium, calcium and magnesium salts of diacetylrhein is carried out by adding to the solution of diacetylrhein, salified with triethylamine, the calculated amount of potassium, calcium, and magnesium,2-ethylhexanoate respectively.

The isolation of the crystalline salts of diacetylrhein takes place by filtration and thereafter a vacuum drying is carried out.

The solubility of the diacetylrhein salts in water is variable and more precisely 1 g of sodium salt of diacetylrbein is soluble in 15 ml of water with a pH of 6.15, 1 g of potassium salt is soluble at pH 6.3 1g of calcium salt is soluble in 500 ml of water at pH of 6.55 and 1 g of magnesium salt is soluble in 350 ml of water with a pH of 6.25.

The following examples are reported hereinbelow for illustrative but non limiting purposes of the present invention.

EXAMPLE 1

To a suspension of 20 g of diacetylrhein in 180 ml of acetone 20 ml of water are added. After the mixture is stirred for 10 minutes a solution of 9 ml of trethylamine in 100 ml of acetone is added at 15°-20° C.

A perfectly clear solution is obtained and 70 ml of a 1 M solution of sodium 2 ethyl-hexanoate in isobutanol are added, diluted with 100 ml of acetone.

The crystallization of the product is left to initiate until the solution begins to become turbid; then the addition of the salifying is prosecuted, it being completed over 90 minutes. After further 30 minutes stirring, the mixture is filtered and washed with acetone . Then it is dried under vacuum at 40° C for 12 hours, and 20.5 g of sodium salt of diacetylrhein are obtained (melting point with decomposition 235° C ).

Analytical data for $C_{19}H_{11}O_8Na$ (MW 390.287)
CALCULATED % C 58.47 H 2.84 Na 5.89

FOUND % C 58.66 H 2.86 Na 5.88
Title (HPLC):94.26% as diacetylrhein (theoretical : 94.36%)

EXAMPLE 2

To a suspension of 36.89 g diacetylrhein in 515 ml of acetone and 36.8 ml of water 16.6 ml of triethylamine are added. The resulting clear solution is treated at 15°–20° C with 128 ml of a 1M solution of potassium −2 ethylhexanoate in isobutanol diluted with 185 ml of acetone.

After adding the potassium 2 ethyl-hexanoate solution until it begins to become turbid, the crystallization is left to initiate and thereafter the addition of the salifying agent is completed over 2 hours.

After further 30 minutes stirring, the crystalline product is filtered washed with acetone and dried under vacuum at 40° C for 12 hours.

35.5 g of diacetylrhein potassium salt are obtained (melting point 210° C with decomposition).

Analytical data for $C_{19}H_{11}O_8K$ (MW 406.395)
CALCULATED % C 56.15 H 2.73 K 9.62
FOUND % C 55.87 H 2.69 K 9.66
Title (HPLC) :89.88% as diacetylrhein (theoretical : 90.63%)

EXAMPLE 3

To a solution of 3.68 g of diacetylrhein in a mixture of 51.5ml of acetone 3.68 ml of water and 1.66 ml of triethylamine are slowly added, at 15°–20° C, 5 ml of 1 M solution of calcium 2-ethylhexanoate in isobutanol diluted with 12.5 ml of acetone. The product is isolated by filtration, washed with acetone and dried under vacuum at 40° C for 12 hours.

There are obtained 3.25 g of calcium salt of diacetylrhein (melting point 260° C with decomposition.)

Analytical data for $(C_{19}H_{11}O_8)_2Ca$ (MW 774,674)
CALCULATED % C 58.92 H 2.86 Ca 5.17
FOUND % C 59.79 H 2.88 Ca 5.22

EXAMPLE 4

A solution of 5.52 g diacetylrhein in a mixture of 77.2 ml of acetone, 5.52 ml of water and 2.49 ml of triethylamine is treated at 15-20° C with 7.5 ml of a 1 M solution of magnesium 2-ethylhexanoate in isobutanol diluted with 19.7 ml of acetone. The crystalline product is isolated by filtration, washed and dried under vacuum at 40° C for 12 hours. There are obtained 4.88 g of magnesium salt of diacetylrhein (melting point 220° C with decomposition).

Analytical data for $(C_{19}H_{11}O_8)_2Mg$ (MW 758.899)
CALCULATED % C 60.14 H 2.92 Mg 3.20
FOUND % C 59.96 H 2.90 Mg 3.17

EXAMPLE 5

To a suspension of 14.72 g of diacetylrhein in 220 ml of acetone and 14.8 ml of water 6.64 ml of triethylamine are added. The resulting clear solution is treated with a solution of 6.24 g of sodium acetate trihydrate in 5.2 ml of water. Succesively 110 ml of acetone are added and the product is isolated by filtration, washed with acetone and dried under vacuum at 40° C for 12 hours. 12.8 g are obtained of sodium salt of diacetylrhein.

EXAMPLE 6

A suspension of 3.68 g of diacetylrhein in 55 ml of acetone and 3.7 ml of water is treated with 1.66 ml of triethylamine. To the resulting clear solution a solution of 1.42 g of potassium carbonate in 1.5 ml of water is added. After addition of 27.5 ml of acetone, the crystalline product is filtered, washed with acetone and dried under vacuum at 40° C for 12 hours.

3.2 g of potassium salt of diacetylrhein are obtained.

EXAMPLE 7

2 ml of an aqueous solution containing 25 mg of potassium diacetyl rhein salts (ARTRODAR K ®) were injected in the sinovial liquid of 20 patients affected by gonarthrosis once a week for five times.

The clinical evaluations obtained after the treatment with potassium diacetylrhein salts are defined as excellent in 8 cases (40%), good in 4 cases (20%), fair in 4 cases (20%), absent in 3 cases (15%), poor in 1 case(5%) the therapeutic method was clearly effective for 80% of the cases treated.

EXAMPLE 8

The same quantity of the aqueous solution used in example 7 and containing the same amount of ARTRODAR K ® was administered in the sinovial liquid of other 20 patients affected by gonarthrosis once a week for 5 times.

The clinical evaluations obtained after the treatment with potassium diacetylrhein salts are defined as excellent in 15 cases (75%),good in 2 cases (10%), absent in 3 cases(15%), the therapeutic method was clearly effective for 85% of the cases treated.

EXAMPLE 9

The same quantity of the aqueous solution used in example 7 and containing the same amount of ARTRODAR K ® was administered in the sinovial liquid of other 20 patients affected by gonarthrosis once a week for 6 times.

The clinical evaluations obtained after the treatment with potassium diacetylrhein salts are defined as excellent in 4 cases (20%), good in 7 cases (35%), fair in 1 case (5%), poor in 3 cases (15%). absent in 1 case (5%).

The therapeutic method was clearly effective for 60% of cases.

EXAMPLE 10

The same quantity of the aqueous solution used in example 7 and containing the same amount of ARTRODAR K ® was administered on the sinovial liquid of other 8 patients affected by gonarthrosis once a week for 5 times.

The clinical evaluations obtained after the treatment with potassium diacetylrhein salts are defined as good in 2 cases (25%), fair in 4 cases (50%), poor in 2 cases (25%).

The therapeutic method was clearly effective for 75% of cases.

COMPARATIVE EXAMPLE 20 patients affected by gonarthrosis were treated with diacetyl rhein (ARTRODAR ®) with the following posology 1×25 mg capsules /day for 4 weeks, and then 1×2 50 mg capsules/ day for further 8 weeks.

The clinical evaluations obtained after the treatment with potassium diacetylrhein salts are defined as excellent in 5 cases ( 25%) good in 12 cases (60%), fair in 2 cases (10%), and poor in 1 case (5%).

The therapeutic method was clearly effective for 95 % of cases.

We claim:

1. A therapeutic method for the treatment of arthrosis diseases comprising administering by intraarticular route from 1 to 5 ml of an aqueous solution containing from 10 to 50 mg of diacetylrhein salts having the general formula (I)

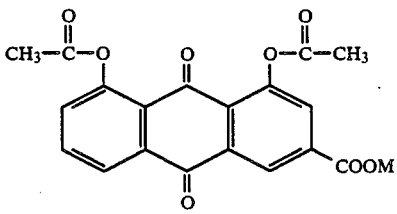

wherein M represents an alkali or an earth alkali metal or the residue of an organic base.

2. The therapeutic method according to claim 1 comprising administering 2ml of an aqueous solution containing 25 mg of diacetylrbein potassium salts once a week for 5-6 times.

* * * * *